(12) United States Patent
Dinh et al.

(10) Patent No.: US 6,168,619 B1
(45) Date of Patent: Jan. 2, 2001

(54) INTRAVASCULAR STENT HAVING A COAXIAL POLYMER MEMBER AND END SLEEVES

(75) Inventors: Linh Dinh, Santa Clara; Beren Correa; Paul Cherkas, both of San Jose; Angelica Alvarado, Santa Clara; Irina D. Pomerantseva, Mountain View; Sudha Thakur; Robert Eury, both of Cupertino; Michael Froix, Mountain View, all of CA (US)

(73) Assignee: Quanam Medical Corporation, Santa Clara, CA (US)

( * ) Notice: Under 35 U.S.C. 154(b), the term of this patent shall be extended for 0 days.

(21) Appl. No.: 09/173,819

(22) Filed: Oct. 16, 1998

(51) Int. Cl.[7] .................................................. A61F 2/06
(52) U.S. Cl. ......................................... 623/1.13; 623/1.28
(58) Field of Search ........................... 623/1, 12, 1.13, 623/1.16, 1.28; 606/195, 198

(56) References Cited

U.S. PATENT DOCUMENTS

| 5,163,952 | * | 11/1992 | Froix ........................................... 623/1 |
| 5,314,688 | * | 5/1994 | Kauffman et al. ................ 424/423 X |
| 5,522,881 | * | 6/1996 | Lentz ........................................... 623/1 |
| 5,628,786 | | 5/1997 | Banas et al. . |
| 5,667,523 | * | 9/1997 | Bynon et al. ...................... 606/198 X |
| 5,700,285 | * | 12/1997 | Myers et al. ............................... 623/1 |
| 5,716,981 | * | 2/1998 | Hunter et al. ...................... 514/449 X |
| 5,723,003 | * | 3/1998 | Winston et al. ........................... 623/1 |
| 5,749,880 | | 5/1998 | Banas et al. . |
| 5,788,626 | | 8/1998 | Thompson . |
| 5,843,164 | * | 12/1998 | Frantzen et al. ........................... 623/1 |
| 5,941,895 | * | 8/1999 | Myler et al. ...................... 606/195 X |
| 5,972,027 | * | 10/1999 | Johnson ................................... 623/1 |

FOREIGN PATENT DOCUMENTS

| WO 95/05555 | 2/1995 | (WO) . |
| WO 96/00103 | 1/1996 | (WO) . |
| WO 98/00090 | 1/1998 | (WO) . |
| WO 98/23299 | 6/1998 | (WO) . |

* cited by examiner

Primary Examiner—V. Millin
Assistant Examiner—Hieu Phan
(74) Attorney, Agent, or Firm—Judy M. Mohr; Iota Pi Law Group

(57) ABSTRACT

A radially-expandable stent for insertion into a lumen is described. The stent is composed of a radially-expandable support stent and a polymer tubular member co-axially disposed over the support stent. Tubular end sleeves are disposed around the first and second ends of the polymer-surrounded support stent to secure the tubular member and to provide other improvements.

77 Claims, 6 Drawing Sheets

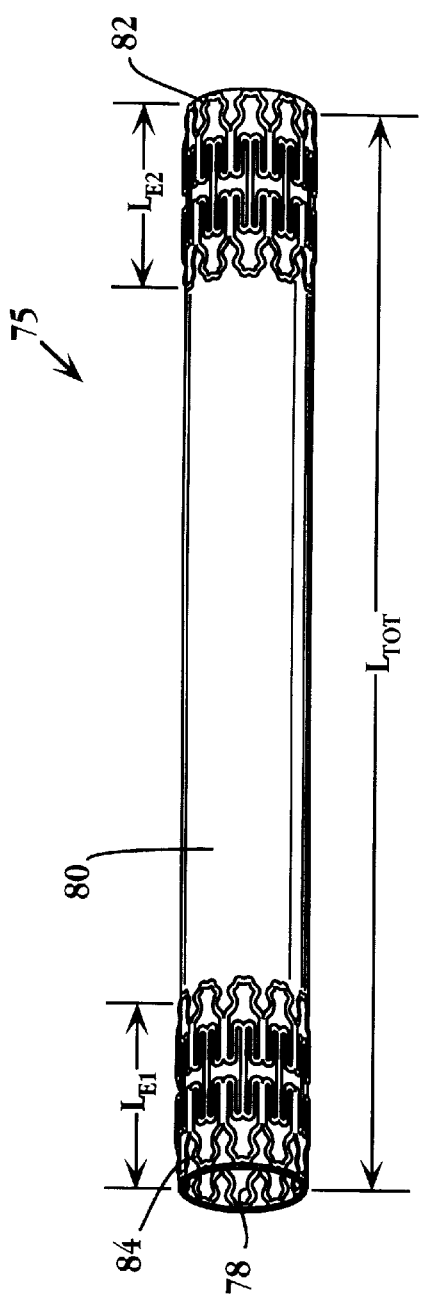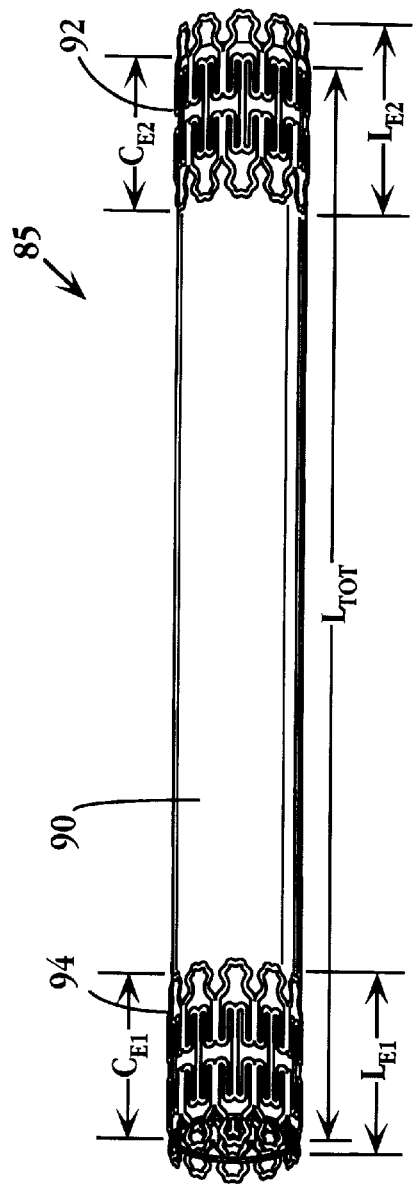

INTRAVASCULAR STENT HAVING A COAXIAL POLYMER MEMBER AND END SLEEVES

FIELD OF THE INVENTION

The present invention relates generally to radially expandable stents for insertion into a body lumen. More particularly, the invention relates to an endoluminal stent having a polymer tubular member secured to the support stent with end sleeves.

BACKGROUND OF THE INVENTION

Endoluminal stents, particularly endovascular stents, are of considerable interest in the medical profession, especially to vascular surgeons. Such stents are presently used as a post-angioplasty adjunct to maintain the angioplasty-treated blood vessel in an open condition. Examples of endoluminal stents in the art include pressure-expandable stents which radially expand using a balloon angioplasty catheter, such as the Palmaz stent in U.S. Pat. No. 4,733,665; or self-expanding stents which radially expand due to the inherent spring tension of a wire material, such as the stent described by Gianturco in U.S. Pat. No. 4,580,568. Self-expanding stents which expand upon application of a stimulus, such as Nitinol stents or shape-memory polymer stents that expand when exposed to an increase in temperature, have also been described (Froix, U.S. Pat. No. 5,163,952).

In some applications it is desirable to cover the stent with a biocompatible material, since the stents themselves are often thrombogenic and the open nature of the stents can result in growth of tissue through the stent and into the lumen causing occlusion. Polytetrafluoroethylene (PTFE) has been proposed as a material suitable for such a covering since PTFE is inert, eliciting less of a foreign body response and less of an immunogenic response, and is largely non-thrombogenic. A variety of PTFE-covered stents are reported in the literature and include a basic stent or graft with an external or internal liner which expands in association with the stent (Myers, U.S. Pat. No. 5,700,285; Thompson, U.S. Pat. No. 5,788,626; Colone, WO 96/00103). In these stent/PTFE covering assemblies, the PTFE covering is typically a tubular member that is slipped over the stent and is held in place with an adhesive. This assembly suffers from a number of disadvantages, including the unequal expansion of the stent and the PTFE covering in the axial direction, leaving the ends of the stent exposed. Another disadvantage is uneven expansion of the assembly in the radial direction along the length of the assembly. During expansion with a balloon angioplasty catheter, the balloon expansion forces the stent and the PTFE covering into a torroidal shape with the proximal and distal ends flaring away from the central longitudinal axis of the stent. This results in the stent being non-uniformly radially expanded along its longitudinal axis.

One approach proposed for overcoming this uneven expansion is to include a reinforcing member along the length of the stent-PTFE covering assembly (Banas, U.S. Pat. No. 5,628,786). The reinforcing member evens the resistance to expansion along the length of the assembly. Disadvantages to such a reinforcing member include an increase in profile of the assembly, an increase in the stiffness and loss of flexibility of the assembly, all of which make it difficult to position the assembly in small or difficult to reach lumens

SUMMARY OF THE INVENTION

Accordingly, it is an object of the invention to provide a stent having a polymer covering, where the assembly retains flexibility and a low profile.

It is a further objective of the invention to provide a stent having a polymer covering with an improved uniformity of expansion.

In one aspect, the invention includes a radially-expandable stent for insertion into a lumen. The stent is composed of a radially-expandable support stent having a selected axial length and having first and second ends. A polymer tubular member is co-axially disposed over the support stent and extends the length of the stent. The polymer member is radially expandable with the support stent to an expanded diameter. The stent is further composed of tubular end sleeves disposed around the first and second ends of the polymer-surrounded support stent, the end sleeves being radially expandable with the support stent to an expanded diameter and covering 50% or less of the total stent length.

In one embodiment, the support stent is composed of a biocompatible metal, such as stainless steel, titanium, tungsten, tantalum, gold, platinum, cobalt, iridium and alloys of these materials. In another embodiment, the metal is a shape-memory alloy.

In another embodiment, the support stent is composed of a polymer, such as a memory polymer. For example, the memory polymer is, in one embodiment, formed of a copolymer.

The polymer tubular member is secured in an unexpanded diameter to the support stent by a mechanical means selected from ultrasonic welding, resistive heating and laser irradiation. Alternatively, the polymer tubular member is secured to the support stent in an unexpanded diameter by a biocompatible adhesive, such as a fluorinated thermoplastic polymer adhesive. Examples of fluorinated thermoplastic include fluorinated ethylene/propylene copolymers, perfluoroalkoxy fluorocarbons, ethylene/tetrafluoroethylene copolymers, fluoroacrylates, and fluorinated polyvinyl ethers.

The polymer tubular member, in one embodiment, is composed of a polymer selected from the group consisting of polyamides, polyimides, silicones and fluorinated polyolefins. A preferred fluorinated polyolefin is polytetrafluoroethylene, which can be either biaxially oriented polytetrafluoroethylene or uniaxially oriented polytetrafluoroethylene. In one embodiment, the polytetrafluoroethylene tubular member has a porosity of at least about 5% and the member further includes a therapeutic agent incorporated into the pores.

In yet another embodiment of the invention, the polymer member of the stent further includes a therapeutic agent. The therapeutic agent is, in one embodiment, an agent effective to inhibit smooth muscle cell proliferation. In other embodiment, the therapeutic agent is an agent effective to inhibit proliferation or migration of fibroblast cells. In another embodiment, the polymer member includes a combination of therapeutic agents, such as a first agent paclitaxel and a second therapeutic agent of camptothecin, colchicine or dexamethasone.

The end sleeves in the stent are composed of a biocompatible metal, such as stainless steel, titanium, tungsten, tantalum, gold, platinum, cobalt, iridium and alloys of these materials. Alternatively, the end sleeves are composed of a shape-memory alloy. Where the end sleeves are composed of metal, the metal is, in one embodiment, coated with polytetrafluoroethylene.

The end sleeves in yet another embodiment are composed of a polymer, such as an elastic polymer, a thermoplastic polymer or a memory polymer. The polymer can be a homopolymer, a copolymer or a polymer blend.

The end sleeves are secured on the ends of the polymer-covered support stent by a mechanical means or by a biocompatible adhesive.

In another aspect, the invention includes an improvement in a stent of a selected axial length and having a polymer tubular member coaxially disposed about the stent. The improvement comprises tubular end sleeves disposed around each end of the stent, the end sleeves being radially expandable with the stent to an expanded diameter, and where the end sleeves cover 50% or less of the total stent length.

In another aspect, the invention includes a method of preparing a stent for insertion into a lumen, comprising providing a radially expandable support stent of a selected axial length and having first and second ends and placing a polymer tubular member co-axially over the support stent. The polymer tubular member, in one embodiment, extends substantially the length of the support stent. The polymer member is radially expandable with the support stent to an expanded diameter. The tubular end sleeves are secured around the first and second ends of the polymer-surrounded support stent. The end sleeves are radially expandable with the support stent to an expanded diameter and the end sleeves cover 50% or less of the total stent length.

In another aspect, the invention includes a method for achieving substantially uniform radial expansion in a stent of a selected axial length and having a polymer tubular member coaxially disposed about the stent. The method includes providing tubular end sleeves disposed around each end of the stent, the end sleeves being radially expandable with the stent to an expanded diameter and covering 50% or less of the total stent length.

These and other objects and features of the invention will be more fully appreciated when the following detailed description of the invention is read in conjunction with the accompanying drawings.

BRIEF DESCRIPTION OF THE DRAWINGS

FIGS. 6A–6B are views of stents in accordance with the invention showing dimensions of the end sleeves relative to the length of the stent.

DETAILED DESCRIPTION OF THE INVENTION

Figure 1A:
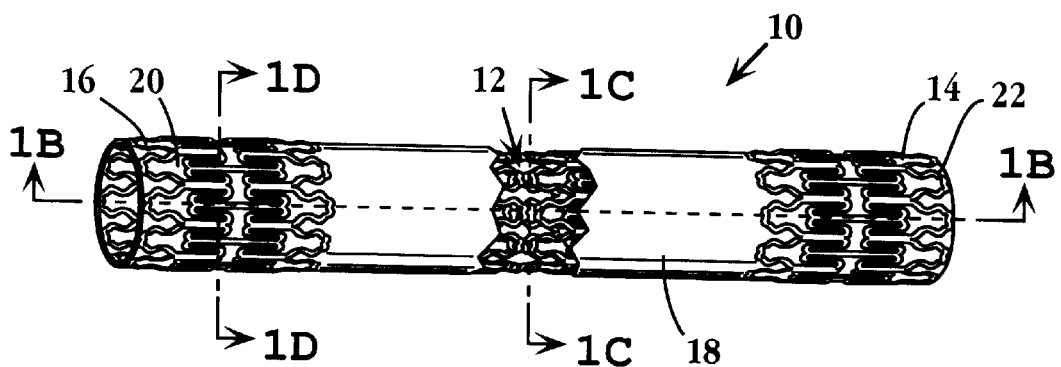
FIG. 1A is a perspective view of a stent in accordance with the invention comprising a support stent with a tubular PTFE member and end sleeves.

Referring now to the accompanying drawings, a preferred embodiment of the stent of the present invention is illustrated in FIG. 1A. Stent 10 generally consists of a support stent 12, visible through the cut-away portion in the drawing, having a first end 14 and a second end 16. The stent, which will be described in more detail below, is radially expandable for insertion into a body lumen in a small-diameter contracted condition and, after placement at a treatment site in a lumen, expansion into a large diameter condition. Support stent 12 is of a selected axial length determined according to the size of the lesion or area in the lumen to be stented.

Stent 10 further consists of a tubular member 18 which is coaxially disposed over support stent 12 and extends the length of the support stent. The tubular member is radially expandable for expansion with the support stent to a large diameter condition. The tubular member in a preferred embodiment is composed of polytetrafluoroethylene (PTFE), but can be composed of other biocompatible materials, such as polyamides, polyimides, silicones, acrylates, methacrylates or other fluorinated polymers. It will be appreciated that the tubular member can be a homopolymer, a copolymer or a polymer blend. For example, the tubular member can be composed of a copolymer of acrylate and methacrylate, such as those described in U.S. Pat. No. 5,163,952, which is herein incorporated by reference in its entirety.

According to an important feature of the invention, stent 10 further includes a pair of tubular end sleeves 20, 22 positioned on the first and seconds ends 14, 16 of the support stent. The end sleeves are radially expandable and, as will be further discussed below, cover about 50% or less of the total stent length.

Figure 1B:
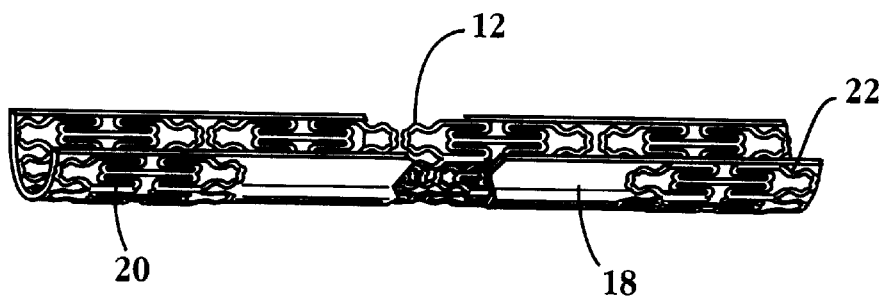
FIG. 1B is a longitudinal cross-sectional view of the stent shown in FIG. 1A taken along line 1B—1B of FIG. 1A.
Figure 1C:
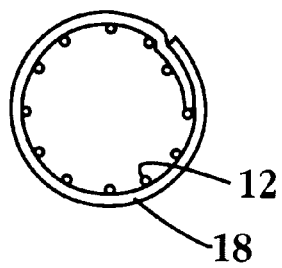
FIGS. 1C–1D are cross-sectional views of the stent shown in FIG. 1A taken along line 1C—1C and line 1D—1D, respectively.
Figure 1D:
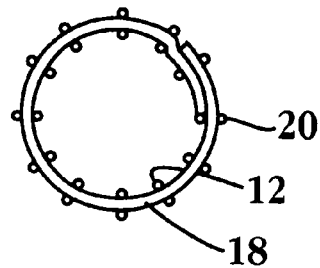

FIG. 1B is a longitudinal cross-sectional view taken along the line 1B—1B in FIG. 1A. The PTFE tubular member 18 circumferentially covers at least a substantial longitudinal aspect of support stent 12, which is visible along the inner portion of the assembly and in the cut-away portion of the tubular member. The end sleeves 20, 22 are disposed about the outer circumference of the ends of the PTFE-covered support stent. FIGS. 1C–1D provide cross-sectional views of the stent of FIG. 1A, taken along lines 1C—1C and 1D—1D, respectively. In FIG. 1C, the support stent 12 and the tubular member 18 are visible. In FIG. 1D, the view provides a cross-sectional perspective of the assembly including an end sleeve 20.

Each of the elements of stent 10, namely, the support stent, the tubular member and the end sleeves will now be discussed with reference to FIGS. 2–4.

The support stent is a cylindrical or tubular in shape and is capable of being implanted into a body lumen in a collapsed or small-diameter condition and then expanded to a larger diameter condition upon placement at the site to be treated. Stents known in the art and suitable for use in the present invention include pressure-expandable stents, self-expanding stents and stents which expand in response to an applied stimulus, such as heat. An exemplary pressure-expanding stent is described in U.S. Pat. Nos. 4,776,337 and 4,733,665 to Palmaz. Pressure-expandable stents are typically radially expanded by means of a balloon angioplasty catheter, as is known in the art. Self-expanding stents, such as the stent described by Gianturco in U.S. Pat. No 4,580,568 and by Wallsten in U.S. Pat. No. 4,544,771, radially expand due to the inherent spring tension of the stent. The stents expand to a larger diameter after being released from a constraining force which restricts it to a smaller diameter. Another sort of self-expanding stent includes stents made of shape-memory material, such as nitinol or shape-memory polymers described by Froix in U.S. Pat. No. 5,163,952. These stents expand upon application of a stimulus, typically an increase in temperature that invokes a phase transition in the material.

Accordingly, the support stent for use in the invention, be it a self-expanding or pressure-expandable stent, can take a variety of configurations and can be composed of a variety of biocompatible materials. Suitable materials include metals, such as stainless steel, tungsten, titanium, gold, platinum and tantalum, alloys of these materials and others, as well as shape-memory alloys, high strength thermoplastic polymers, copolymers, including shape-memory polymers.

Figure 2:
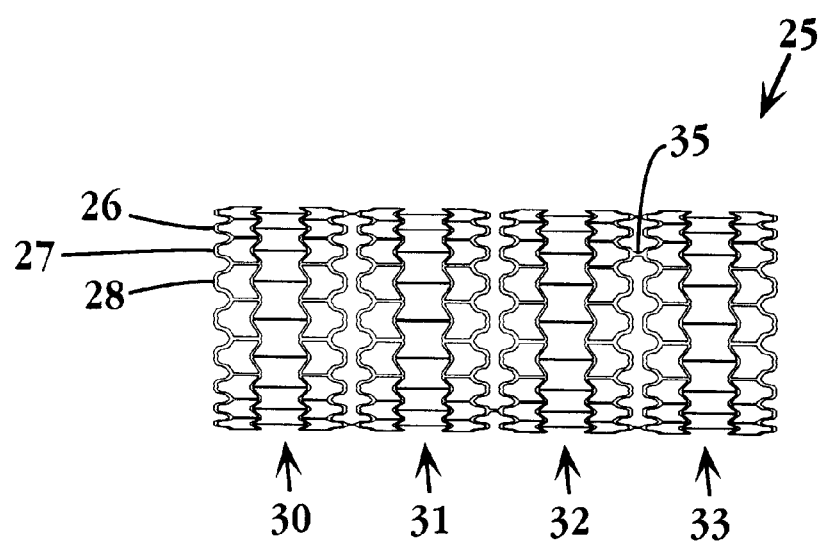
FIG. 2 shows a stent suitable for use as a support stent in the stent of the invention.

In a preferred embodiment, the support stent is composed of a metal, such as stainless steel, and has the configuration shown in FIG. 2. Support stent 25 is a pressure-expandable stent and is shown in FIG. 2 in an expanded, large diameter condition. The stent is composed of unit cells, such as unit cells 26, 27, 28, joined in a radial direction to form a plurality of unit cells 30. Support stent 25 as shown is composed of four pluralities of unit cells, 30, 31, 32 and 33. The pluralities of unit cells are joined radially by a connecting segment, such as connecting segment 35 which joins pluralities 32, 33. Each unit cell is expandable to move the stent from a small-diameter condition, for insertion into a body lumen, to a large-diameter condition, for deployment into the body lumen. The stent of FIG. 2 is described in detail in co-pending application Ser. No. 09/053,887, filed Apr. 1, 1998, which is herein incorporated by reference.

Figure 3:
FIG. 3 is a perspective view of the tubular member prior to placement over a support stent.

The polytetrafluoroethylene tubular member carried coaxially about the outer circumference of the support stent is shown in FIG. 3. Tubular member 40 as shown in FIG. 3 takes the form of a flat sheet rolled into a cylindrical or tubular shape by overlapping the edges 42, 44 of the sheet It will be appreciated that the initial configuration of the tubular member is not limited to a flat sheet, but can also be prepared from an extruded tube-form. As mentioned above, in a preferred embodiment, the tubular member is composed of PTFE, and can be of biaxially oriented PTFE or of uniaxially oriented PTFE. The tubular member is formed, as shown in the embodiment of FIG. 3, from a polytetrafluoroethylene sheet which is wrapped into a cylinder having the desired diameter and is then sealed along the overlapping edges. The overlapping edges of the PTFE-tubular member are secured in their unexpanded, small-diameter condition by a mechanical means or by a chemical means. Examples of mechanical means include ultrasonic welding, resistive heating or laser irradiation. A preferred example of a chemical means is a biocompatible adhesive, such as a fluorinated thermoplastic polymer including fluorinated ethylene/propylene copolymers (FEP) such as tetrafluoroethylene/hexafluoropropylene, perfluoroalkoxy fluorocarbons (PFA), such as tetrafluoroethyl/perfluoroethylene copolymers (ETFE), ethylene/tetrafluoroethylene copolymers, fluoroacrylates and fluorinated polyvinyl ethers.

The PTFE tubular member is, in another embodiment, secured to the support stent using such a biocompatible adhesive. The inner surface of the tubular member which contacts the support stent can be coated with a layer of the adhesive prior to placing the member over the support stent.

In another embodiment of the invention, the tubular member is composed from PTFE having a selected porosity, preferably of at least about 5% and up to 80–90% porosity. The pores in the PTFE member are filled with a therapeutic agent for administration of the agent at the target site in a lumen. In practice, the tubular member can be soaked in a solution containing the agent to fill the pores with the drug-containing solution. The solvent can then be removed by heating or reducing pressure. Therapeutic agents contemplated for use include, but are not limited to, agents effective to inhibit or reduce smooth muscle proliferation and/or agents effective to inhibit or reduce proliferation or migration of fibroblast cells. Examples of such agents include paclitaxel and its derivatives, colchicine and DNA oligonucleotides, such as those oligonucleotides described in WO 98/23229. Other exemplary agents include anticoagulants, antiplatlet agents and antibacterial agents. Specific preferred agents include heparin, warfarin, low molecular weight heparin, hirudin, glucocorticoids, angiotensin converting enzyme inhibitors, vincristine, actinomycin, and platelet derived growth factor. Another preferred group of agents is topoisomerase inhibitors, including compounds having activity against topoisomerase I and topoisomerse II enzymes as well as agents having combined activity against both topoisomerase I and II. A preferred topoisomerase I inhibitor is camptothecin and analogues of camptothecin. Other contemplated agents include vascular endothelial growth factor (VEGF), thrombolytic agents, such as streptokinase, urokinase, and tissue plasminogen activator (TPA).

Figure 4A:
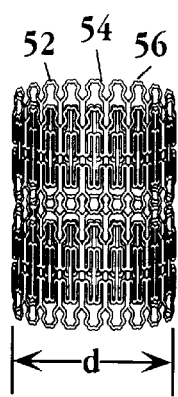
FIGS. 4A–4C illustrate various configurations of end sleeves suitable for use in the stent of the invention, where the end sleeves are shown in a small-diameter unexpanded condition.
Figure 4B:
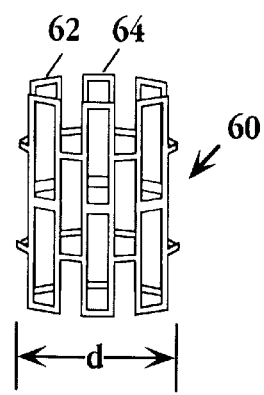
Figure 4C:
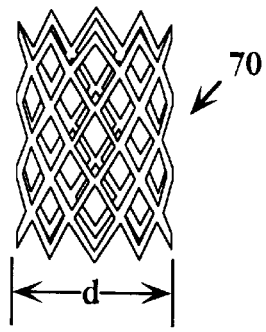
Figure 5A:
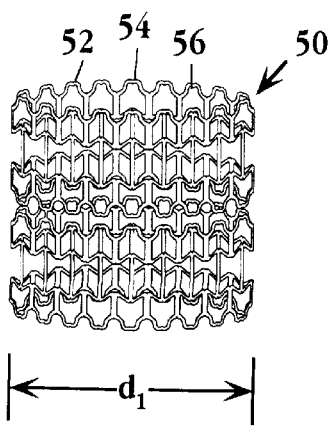
FIGS. 5A–5C illustrate the end sleeves of FIGS. 4A–4C, respectively, where the sleeves are shown in their large-diameter, expanded conditions.
Figure 5B:
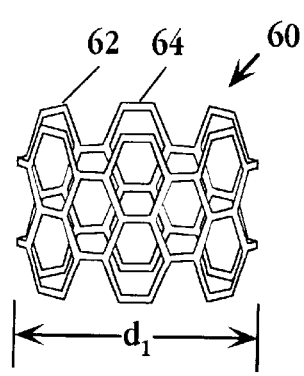
Figure 5C:
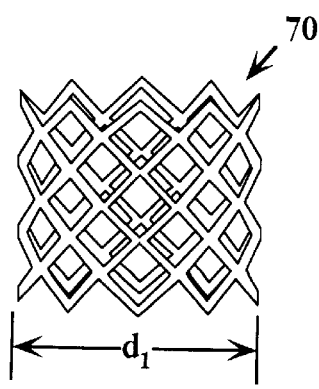

Turning now to FIGS. 4A–4C and FIGS. 5A–5C, various configurations of the end sleeves for use in the stent are illustrated. Each of the end sleeves in FIGS. 4A–4C are shown in a small diameter condition prior to expansion for deployment at a target site in a lumen. FIGS. 5A–5C shown the end sleeves of FIGS. 4A–4C in their expanded, large diameter condition, after deployment at a target site.

FIG. 4A shows an end sleeve 50 composed of unit cells, such as unit cells 52, 54, 56, like those described above in FIG. 2. The unit cells are expandable to move the stent from a small-diameter condition d, as shown in FIG. 4A to a large-diameter condition $d_1$, as shown in FIG. 5A, upon application of a radially outwardly extending force, such as supplied by a balloon of a balloon catheter.

FIG. 4B shows another configuration suitable for use as an end sleeve in the stent of the invention. Sleeve 60 consists of a plurality of elongate members, such as members 62, 64, made of thin bars with openings between the members. The expanded configuration of sleeve 60 of FIG. 4B is shown in FIG. 5B.

FIG. 4C shows another configuration of an end sleeve for use in the PTFE-covered stent of the invention. Sleeve 70 takes the form of a wire mesh, and is shown in a small-diameter condition d in FIG. 4C and in its large-diameter condition $d_1$ condition in FIG. 5C.

The end sleeves are composed of a biocompatible material, including metals, alloys and polymers. Suitable metals include stainless steel, titanium, tungsten, tantalum, gold, platinum, cobalt, iridium and alloys of these. The metal can be coated with a biocompatible polymer, such as polytetrafluoroethylene. In another embodiment, the end sleeves are composed of a polymer, including elastic polymers, thermoplastic polymers, copolymers and memory polymers.

The end sleeves are secured on the PTFE-covered stent typically by the nature of a secure fit. That is, the end sleeves are dimensioned to fit snugly over the PTFE-covered stent. It will be appreciated that in some applications it may be desired to secure the end sleeves with a restraining device or with an adhesive, such as those described above.

A PTFE-covered stent 75 of total length $L_{TOT}$ is shown in FIG. 6A. Support stent 78 is shown in an unexpanded condition for insertion into a body lumen. Coaxial with stent 78 is a PTFE tubular member 80, also having a length $L_{TOT}$.

The end sleeves 82, 84 are disposed about the ends of the PTFE-covered support stent and, as will be appreciated, can vary in length $L_{E1}$, and $L_{E2}$. In accordance with a feature of the invention, the dimension ($L_{E1}$+$L_{E2}$) covers no more than about 50% of the total stent length $L_{TOT}$. For example, for a stent having a total length of 15 mm, the end sleeves, if equal in length, would be no longer than 3.75 mm each, for a combined length of the end sleeves ($L_{E1}$+$L_{E2}$) of 7.5 mm, which is 50% of the 15 mm total length. Of course, the end sleeves can be smaller than 3.75 mm, as small as 5% or less of the total stent length, the lower limit for size being primarily dictated by functionality. Namely, the end sleeves should be sufficient in length to secure the PTFE tubular member about the support stent and to provide for more uniform expansion of the stent. The upper length limit of the end sleeves is in part determined by the desired flexibility of the stent and by the desired operating pressure for expansion of the stent, where increasing the length of the end sleeves decreases flexibility and increases the pressure needed to fully expand the stent.

In another embodiment, the end sleeves extend from the PTFE-covered stent, as shown in FIG. 6B. Stent 85 includes a support stent which is not visible in the figure, with a coaxial PTFE tubular member 90. Tubular member 90 in this embodiment has a length less than the total stent length, $L_{TOT}$. End sleeves 92, 94 are disposed on either end of the PTFE-covered stent and, as seen, extend from the ends of the stent. As in the embodiment of FIG. 6A, the end sleeves in contact with the PTFE-covered stent is less than about 50% of the total stent length. It will be appreciated that, in this embodiment, the sum of the lengths of each end sleeve, ($L_{E1}$+$L_{E2}$) may exceed 50% of the total length, $L_{TOT}$. However, the sum of the portions of the end sleeve in contact with the PTFE-stent, $C_{E1}$+$C_{E2}$, does not exceed 50% of the total stent length.

In studies performed in support of the invention, a stent as shown in FIG. 6B was prepared, where the total stent length was about 13 mm. A PTFE tubular member composed of a medical grade, commercially available polytetrafluoroethylene having a porosity of 80% was according to one of the methods set forth in Example 1. End sleeves having a length of 4 mm were placed over each end of the PTFE-covered stent in such a way that only 2 mm of each sleeve was in contact with the PTFE member, and 2 mm of each sleeve extended from the end of the PTFE-covered stent, as depicted in FIG. 6B. The stent was placed over the balloon portion of a balloon catheter and inflated. Importantly, the stent expanded to its large diameter condition at a pressure required to expand the support stent alone. That is, the end sleeves while serving to secure the PTFE tubular member and prevent it from "bunching" up during insertion in a lumen and to provide for more uniform expansion, offer relatively little resistance to expansion. This is important because large pressures for expansion of the stent are undesirable from a safety point of view.

FIGS. 7A–7D illustrate introduction, expansion and deployment of the stent of the invention in a body lumen. It will be appreciated that the stent of the invention is suitable for use in a variety of applications, including, but not limited to, prevention of restenosis, reinforcement of reopened, previously obstructed bile ducts and support of narrowing lumens, such as the esophagus, intestine or urethra.

Figure 7A:
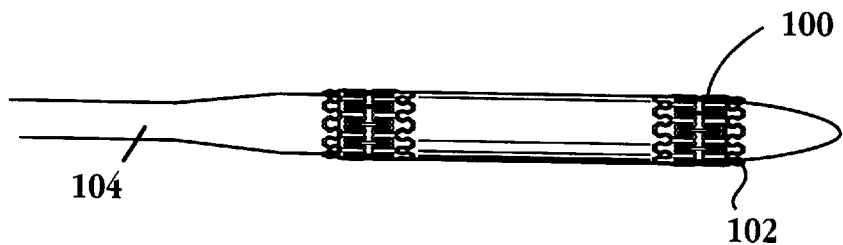
FIGS. 7A–7D illustrate placement of a stent according to the invention over a balloon of a catheter and insertion and deployment of the stent into a lumen.

With initial reference to FIG. 7A, a stent 100 is mounted on a balloon portion 102 of a catheter 104. The stent is secured on the catheter by simply compressing it in place for a snug fit over the balloon. Other means to secure the stent to the balloon include temporary adhesives or a withdrawable sleeve, or through ridges or collars on the balloon to restrain lateral movement of the stent.

Figure 7B:
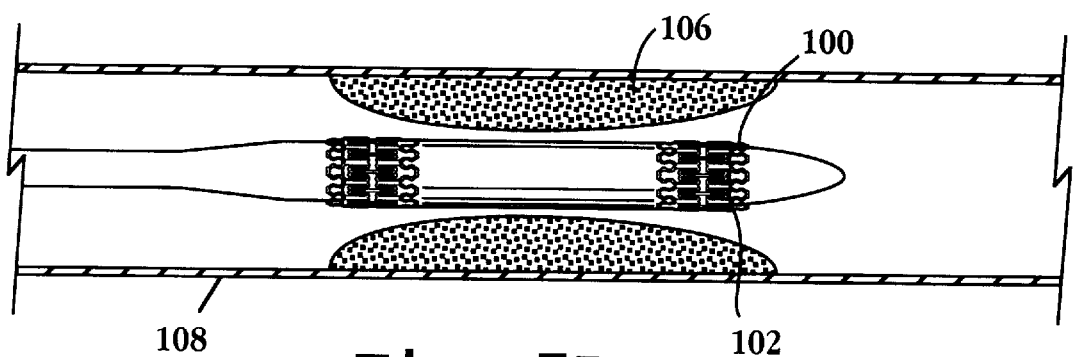
Figure 7C:
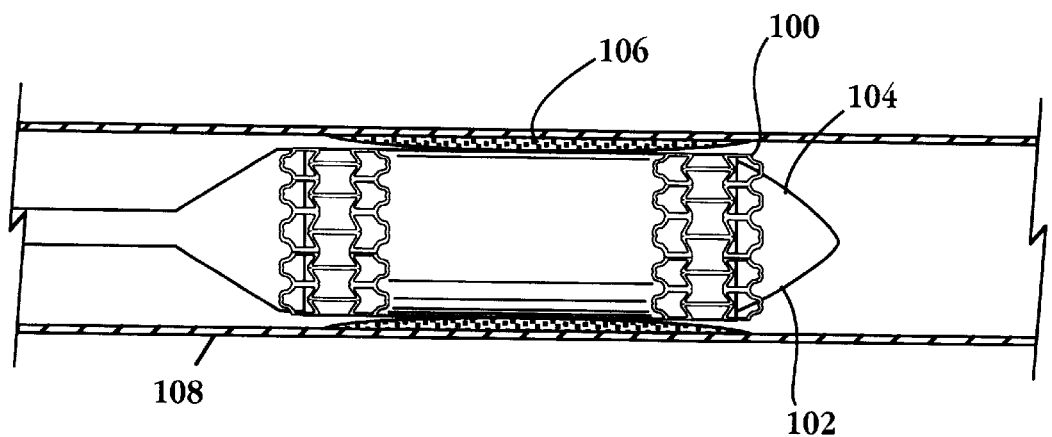

The catheter-stent assembly of FIG. 7A is then advanced through a body lumen of a patient to a treatment site, as shown in FIG. 7B. Once balloon 102 is positioned at the site it is to be implanted, typically across a lesion such as a plaque deposit 106 within a vessel 108, the balloon portion of the catheter is inflated by known means, as depicted in FIG. 7C. The inflation of the balloon causes expansion of the stent from its small-diameter, unexpanded condition of FIG. 7A to its larger-diameter, expanded condition. The stent radially expands and presses against the lesion, contacting the vessel wall and exerting a radial pressure on the vessel wall.

Figure 7D:
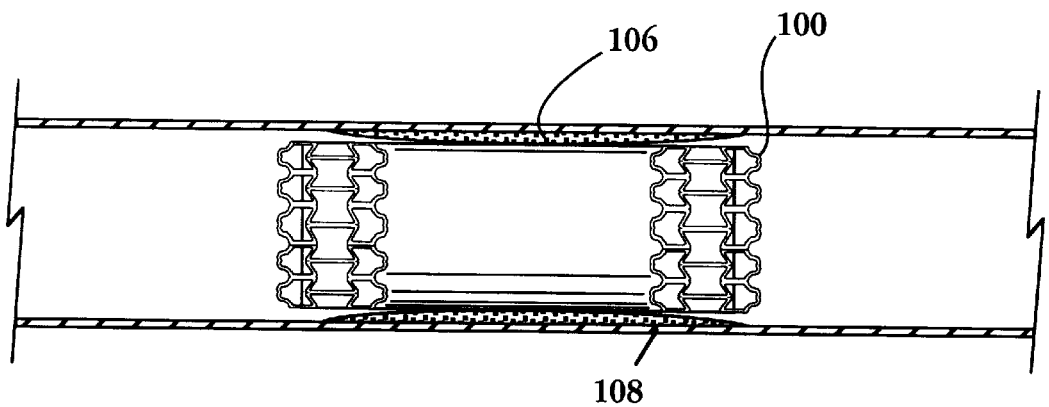

The balloon is then deflated and the catheter is removed from the vessel. The stent remains in its expanded form within the vessel, as shown in FIG. 7D, to prevent reclosure or obstruction of the vessel.

From the foregoing, it can be appreciated how various features and objects of the invention are met. The PTFE tubular member covering the support improves biocompatibility of the support stent. The end sleeves disposed on each end of the PTFE-covered support stent secure the PTFE tubular member about the stent, ensuring that the PTFE member does not slip or bunch-up during insertion into a lumen via a catheter. The end sleeves further provide for more uniform expansion along the longitudinal aspect of the stent, preventing the ends from flaring during expansion. These improvements offered by the end sleeves are achieved with no loss in flexibility of the stent, so that placement of the PTFE-covered stent in small, tortuous vessels is possible. Further, the improvements are achieved with no appreciable increase in the pressure needed to expand the stent to its large-diameter condition for placement in a target lumen.

EXAMPLES

The following example illustrates methods of preparing the stent in accordance with the invention. The example is intended to be illustrative and in no way limiting to the invention.

Example 1

PREPARATION OF A STENT

Method A. A rectangular sheet of expanded PTFE having dimensions of 0.28 inches (extrusion direction) and 0.512 inches (transverse direction) was cut. These dimensions are suitable for use with a support stent having a length of 13 mm and an unexpanded diameter of 0.062 inches and an expanded diameter of 3.5 mm.

The PTFE sheet was wrapped lengthwise ¾ of the way around a flat mandrel measuring 0.0745 inches in width by 0.031 inches in thickness by 2 inches in length. A strip of FEP adhesive of dimensions 0.002 inches thick by 0.031 inches wide by 2 inches long was placed between the overlapping edges of the ePTFE sheet. The mandrel with the wrapped, adhesively sealed sheet was placed onto an ultrasonic welder pad, directly centered under the horn. The ultrasonic welder was activated for 110 msec, at a hold time=2.5 sec and an air pressure=30 psi. The tubular member was removed from the mandrel and visually inspected. The weld area should be translucent along its length.

The metal support stent was mounted on a steel mandrel. The tubular member was then slid onto the metal stent so as to be centered lengthwise. End sleeves of the desired dimension were then expanded so as to clear the tubular member.

The end sleeves were slid over the tubular member and positioned such that when they are returned to their original diameter, the alignment between the stent, tubular member, and end sleeves was appropriate. The stent/tubular member/end sleeve combination was then mounted on the balloon of a catheter for insertion into a test animal.

Method B. A rectangular sheet of expanded PTFE having dimensions of 0.34 inches (extrusion direction) and 0.512 inches (transverse direction) was cut. These dimensions are suitable for use with a support stent having a length of 13 mm and an unexpanded diameter of 0.062 inches and an expanded diameter of 3.5 mm.

A metal support stent was mounted on a steel mandrel. The ePTFE sheet was wrapped between 1.5–1.75 times around the circumference of the stent in a manner that centers the resulting tubular member along the length of the stent.

The end sleeves of the selected dimension were then expanded up so as to clear the tubular member and carefully slipped over the tubular member and positioned such that when returned to their original, unexpanded diameter, the alignment between the stent, tubular member, and end sleeves was as desired. The stent/tubular member/end sleeve combination was then mounted on the balloon of a catheter for insertion into a test animal.

Method C: A rectangular sheet of expanded PTFE having dimensions of 0.28 inches (extrusion direction) and 0.512 inches (transverse direction) was cut. These dimensions are suitable for use with a support stent having a length of 13 mm and an unexpanded diameter of 0.062 inches and an expanded diameter of 3.5 mm.

The PTFE sheet was wrapped lengthwise ¾ of the way around a flat mandrel measuring 0.0745 inches in width by 0.031 inches in thickness by 2 inches in length. A strip of FEP adhesive of dimensions 0.002 inches thick by 0.031 inches wide by 2 inches long was placed between the overlapping edges of the ePTFE sheet. The mandrel with the wrapped, adhesively sealed sheet was placed onto an ultrasonic welder pad, directly centered under the horn. The ultrasonic welder was activated for 110 msec, at a hold time=2.5 sec and an air pressure=30 psi. The tubular member was removed from the mandrel and visually inspected. The weld area should be translucent along its length.

The metal support stent was mounted on a steel mandrel. The tubular member was then slid onto the metal stent so as to be centered lengthwise.

The mandrel/stent/tubular member assembly was then exposed to a heat source of appropriate temperature to give a shrinking of the tubular member onto the metal stent. The heat source can be a hot box, oven, or infra-red source. The required temperature for the PTFE was 200° C.

The stent/tubular member combination was then mounted on the balloon of the catheter.

Method D: A rectangular sheet of expanded PTFE having dimensions of 0.48 inches (extrusion direction) and 0.512 inches (transverse direction) was cut. These dimensions are suitable for use with a support stent having a length of 13 mm and an unexpanded diameter of 0.062 inches and an expanded diameter of 3.5 mm.

The PTFE sheet was wrapped lengthwise ¾ of the way around a flat mandrel measuring 0.37 inches in width by 0.031 inches in thickness by 2 inches in length. A strip of FEP adhesive of dimensions 0.002 inches thick by 0.031 inches wide by 2 inches long was placed between the overlapping edges of the ePTFE sheet. The mandrel with the wrapped, adhesively sealed sheet was placed onto an ultrasonic welder pad, directly centered under the horn. The ultrasonic welder was activated for 110 msec, at a hold time=2.5 sec and an air pressure=30 psi. The tubular member was removed from the mandrel and visually inspected. The weld area should be translucent along its length.

The metal support stent was mounted on a steel mandrel. The tubular member was then slid onto the metal stent so as to be centered lengthwise. The tubular member was then "pinched" together to form a tube in intimate contact with the exterior surface of the support stent and a flap of excess material. The flap of excess material was wrapped around the stent.

The end sleeves were then expanded up so as to clear the tubular member and slipped over the tubular member and positioned such that when returned to their original, unexpanded diameter, the alignment between the stent, tubular member, and end sleeves was as desired. The stent/tubular member/end sleeve stent assembly combination was then mounted on the balloon of the catheter.

Although the invention has been described with respect to particular embodiments, it will be apparent to those skilled in the art that various changes and modifications can be made without departing from the invention.

It is claimed:

1. A radially-expandable stent for insertion into a lumen, comprising
   a radially expandable support stent of a selected axial length having first and second ends;
   a polymer tubular member co-axially disposed over the support stent and extending the length of the support stent, the polymer member being radially expandable with the support stent to an expanded diameter and having an internal surface and an external surface, and
   tubular end sleeves having an internal surface and an external surface, said end sleeves being disposed around said first and second ends of the polymer-surrounded support stent with the end sleeves' internal surfaces in contact with the polymer tubular member and the end sleeves' external surfaces exposed, said end sleeves (i) being radially expandable with the support stent to an expanded diameter, and (ii) covering 50% or less of the stent length.

2. The stent of claim 1, wherein the support stent is composed of a biocompatible metal.

3. The stent of claim 2, wherein the metal is selected from the group consisting of stainless steel, titanium, tungsten, tantalum, gold, platinum, cobalt, iridium and alloys of these materials.

4. The stent of claim 2, wherein the metal is a shape-memory alloy.

5. The stent of claim 1, wherein the support stent is composed of a polymer.

6. The stent of claim 5, wherein the polymer is a memory polymer.

7. The stent of claim 6, wherein the memory polymer is formed of a copolymer.

8. The stent of claim 1, wherein the polymer tubular member is formed into a cylindrical shape and secured in the cylindrical shape by joining overlapping edges of the member by a mechanical means selected from ultrasonic welding, resistive heating and laser irradiation.

9. The stent of claim 1, wherein the polymer tubular member is secured to the support stent in an unexpanded diameter by a biocompatible adhesive.

10. The stent of claim 9, wherein the biocompatible adhesive is a fluorinated thermoplastic polymer.

11. The stent of claim 10, wherein the fluorinated thermoplastic is selected from the group consisting of fluorinated ethylene/propylene copolymers, perfluoroalkoxy fluorocarbons, ethylene/tetrafluoroethylene copolymers, fluoroacrylates, and fluorinated polyvinyl ethers.

12. The stent of claim 1, wherein the polymer member is composed of a polymer selected from the group consisting of polyamides, polyimides, silicones, acrylates, methacrylates and fluorinated polyolefins.

13. The stent of claim 1, wherein the polymer member is composed of polytetrafluoroethylene.

14. The stent of claim 13, wherein the polytetrafluoroethylene tubular member is composed of biaxially oriented polytetrafluoroethylene.

15. The stent of claim 13, wherein the polytetrafluoroethylene tubular member is composed of uniaxially oriented polytetrafluoroethylene.

16. The stent of claim 13, wherein the polytetrafluoroethylene tubular member has a porosity of at least about 5% and the member further includes a therapeutic agent incorporated into the pores.

17. The stent of claim 1, wherein the polymer member further includes a therapeutic agent.

18. The stent of claim 17, wherein the therapeutic agent is an agent effective to inhibit smooth muscle cell proliferation.

19. The stent of claim 17, wherein the therapeutic agent is an agent effective to inhibit proliferation or migration of fibroblast cells.

20. The stent of claim 17, wherein the therapeutic agent is selected from the group consisting of anticoagulants, antiplatlet agents, thrombolytic agents and antibacterial agents.

21. The stent of claim 20, wherein the thrombolytic agent is selected from the group consisting of urokinase, streptokinase and tissue plasminogen activator.

22. The stent of claim 17, wherein the agent is paclitaxel or a derivative of paclitaxel.

23. The stent of claim 17, wherein the therapeutic agent is selected from the group consisting of colchicine, heparin, warfarin, low molecular weight heparin, hirudin, glucocorticoids, angiotensin converting enzyme inhibitors, vincristine, actinomycin, platelet derived growth factor, vascular endothelial growth factor and oligonucleotides.

24. The stent of claim 17, wherein the therapeutic agent is a topoisomerase inhibitor.

25. The stent of claim 24, wherein the topoisomerase inhibitor is camptothecin or an analogue of camptothecin.

26. The stent of claim 17, wherein the polymer member includes a second therapeutic agent.

27. The stent of claim 26, wherein the therapeutic agent is paclitaxel and the second therapeutic agent is selected from the group consisting of camptothecin, colchicine and dexamethasone.

28. The stent of claim 1, wherein the end sleeves are composed of a biocompatible metal.

29. The stent of claim 28, wherein the metal is selected from the group consisting of stainless steel, titanium, tungsten, tantalum, gold, platinum, cobalt, iridium and alloys of these materials.

30. The stent of claim 28, wherein the metal is a shape-memory alloy.

31. The stent of claim 28, wherein the metal is coated with polytetrafluoroethylene.

32. The stent of claim 1, wherein the end sleeves are composed of a polymer.

33. The stent of claim 1, wherein the end sleeves are composed of an elastic polymer.

34. The stent of claim 1, wherein the end sleeves are composed of a copolymer.

35. The stent of claim 32, wherein the polymer is a memory polymer.

36. The stent of claim 35, wherein the memory polymer is formed of a copolymer.

37. The stent of claim 1, wherein the end sleeves are secured on the ends of the polymer-covered support stent by a mechanical means.

38. The stent of claim 1, wherein the end sleeves are secured on the ends of the polymer-covered support stent by a biocompatible adhesive.

39. An improvement in a stent of a selected axial length and having a polymer tubular member coaxially disposed about the stent, said improvement comprising tubular end sleeves, each end sleeve having an internal surface and an external surface, said end sleeves being disposed around each end of the stent such that the internal surface of each end sleeve is in contact with the polymer tubular member and the external surface of each end sleeve is exposed, said end sleeves being radially expandable with the stent to an expanded diameter and covering 50% or less of the stent length.

40. A method of preparing a stent for insertion into a lumen, comprising providing a radially expandable support stent of a selected axial length and having first and second ends;

placing a polymer tubular member co-axially over the support stent and extending the length of the stent, the polymer member being radially expandable with the support stent to an expanded diameter, and securing tubular end sleeves around the first and second ends of the polymer-surrounded support stent, said end sleeves each having an internal surface in contact with the polymer tubular member and an external surface exposed, said end sleeves being radially expandable with the support stent to an expanded diameter and covering 50% or less of the stent length.

41. The method of claim 40, wherein said providing includes providing a support stent composed of a biocompatible metal.

42. The method of claim 41, wherein the metal is selected from the group consisting of stainless steel, titanium, tungsten, tantalum, gold, platinum, cobalt, iridium and alloys of these materials.

43. The method of claim 41, wherein the metal is a shape-memory alloy.

44. The method of claim 40, wherein said providing includes providing a support stent composed of a polymer.

45. The method of claim 44, wherein the polymer is a memory polymer.

46. The method of claim 45, wherein the memory polymer is formed of a copolymer.

47. The method of claim 40, wherein the polymer tubular member is formed into a cylindrical shape and secured in the cylindrical shape by joining overlapping edges of the member by a mechanical means selected from ultrasonic welding, resistive heating and laser irradiation.

48. The method of claim 40, wherein said placing of the polymer tubular member includes securing the member to the support stent in an unexpanded diameter by means of a biocompatible adhesive.

49. The method of claim 48, wherein the biocompatible adhesive is a fluorinated thermoplastic polymer.

50. The method of claim 49, wherein the fluorinated thermoplastic is selected from the group consisting of fluorinated ethylene/propylene copolymers, perfluoroalkoxy fluorocarbons, ethylene/tetrafluoroethylene copolymers, fluoroacrylates, and fluorinated polyvinyl ethers.

51. The method of claim 40, wherein said placing includes placing a polymer member composed of a polymer selected from the group consisting of polyamides, polyimides, silicones, acrylates, methacrylates and fluorinated polyolefins.

52. The method of claim 40, wherein said placing includes placing a polytetrafluoroethylene tubular member composed of biaxially oriented polytetrafluoroethylene.

53. The method of claim 40, wherein said placing includes placing a polytetrafluoroethylene composed of uniaxially oriented polytetrafluoroethylene.

54. The method of claim 40, wherein said placing includes placing a polytetrafluoroethylene tubular member having a porosity of at least about 5% and having a therapeutic agent incorporated into the pores.

55. The method of claim 40, wherein said placing includes placing a polymer member including a therapeutic agent.

56. The method of claim 55, wherein the therapeutic agent is an agent effective to inhibit smooth muscle cell proliferation.

57. The method of claim 55, wherein the therapeutic agent is an agent effective to inhibit proliferation or migration of fibroblast cells.

58. The method of claim 55, wherein the therapeutic agent is selected from the group consisting of anticoagulants, antiplatlet agents, thrombolytic agents and antibacterial agents.

59. The method of claim 58, wherein said thrombolytic agent is selected from the group consisting of urokinase, streptokinase and tissue plasminogen activator.

60. The method of claim 55, wherein the agent is paclitaxel or a derivative of paclitaxel.

61. The method of claim 55, wherein the therapeutic agent is selected from the group consisting of colchicine, heparin, warfarin, low molecular weight heparin, hirudin, glucocorticoids, angiotensin converting enzyme inhibitors, vincristine, actinomycin, platelet derived growth factor, vascular endothelial growth factor and oligonucleotides.

62. The method of claim 55, wherein the therapeutic agent is a topoisomerase inhibitor.

63. The method of claim 62, wherein the topoisomerase inhibitor is camptothecin or an analogue of camptothecin.

64. The method of claim 55, wherein the polymer member further includes a second therapeutic agent.

65. The method of claim 64, wherein the therapeutic agent is paclitaxel and the second therapeutic agent is selected from the group consisting of camptothecin, colchicine and dexamethasone.

66. The method of claim 40, wherein said securing includes securing end sleeves composed of a biocompatible metal.

67. The method of claim 66, wherein the metal is selected from the group consisting of stainless steel, titanium, tungsten, tantalum, gold, platinum, cobalt, iridium and alloys of these materials.

68. The method of claim 66, wherein the metal is a shape-memory alloy.

69. The method of claim 66, wherein the metal is coated with polytetrafluoroethylene.

70. The method of claim 40, wherein said securing includes securing end sleeves composed of a polymer.

71. The method of claim 40, wherein said securing includes securing end sleeves composed of an elastic polymer.

72. The method of claim 40, wherein said securing includes securing end sleeves composed of a copolymer.

73. The method of claim 70, wherein the polymer is a memory polymer.

74. The method of claim 73, wherein the memory polymer is formed of a copolymer.

75. The method of claim 40, wherein said securing includes securing the end sleeves on the ends of the polymer-covered support stent by a mechanical means.

76. The method of claim 40, wherein said securing includes securing the end sleeves on the ends of the polymer-covered support stent by a biocompatible adhesive.

77. A method for achieving substantially uniform radial expansion in a stent of a selected axial length and having a polymer tubular member coaxially disposed about the stent, comprising, providing tubular end sleeves disposed around each end of the stent, said end sleeves each having an internal surface in contact with the polymer tubular member and an external surface exposed, said end sleeves being radially expandable with the stent to an expanded diameter and covering 50% or less of the stent length.

* * * * *